(12) United States Patent
Wymann

(10) Patent No.: US 6,358,282 B1
(45) Date of Patent: Mar. 19, 2002

(54) METHOD FOR THE RELEASING OF AN INSERT FROM THE SHELL OF AN ARTIFICAL JOINT PAN AND ARTIFICAL JOINT PAN

(75) Inventor: Burkhard Wymann, Elgg (CH)

(73) Assignee: Sulzer Orthpaedie AG, Baar (CH)

( * ) Notice: Subject to any disclaimer, the term of this patent is extended or adjusted under 35 U.S.C. 154(b) by 0 days.

(21) Appl. No.: 09/415,738

(22) Filed: Oct. 12, 1999

(30) Foreign Application Priority Data

Oct. 23, 1998 (EP) .............................................. 98811065

(51) Int. Cl.⁷ .................................................. A61F 2/32
(52) U.S. Cl. .................................. 623/22.28; 623/22.12
(58) Field of Search ................ 623/22.28, 22.21–22.29, 623/909, 23.43, 22.19, 22.18, 22.17, 22.12; 403/11, 15, 16, 31

(56) References Cited

U.S. PATENT DOCUMENTS 4,738,151 A * 4/1988 Russell et al. ................. 74/431
5,549,709 A * 8/1996 Caspers ........................ 623/24
5,641,323 A   6/1997 Calarise

FOREIGN PATENT DOCUMENTS

| DE | 2139878 | * | 2/1973 | ............... 623/22.28 |
| DE | 29516473 U1 | | 1/1996 | |
| DE | 19611249 A1 | | 9/1997 | |
| DE | 19611250 A1 | | 9/1997 | |
| DE | 19704577 A1 | | 8/1998 | |
| EP | 0826347 A1 | | 3/1998 | |
| FR | 2398490 | | 2/1979 | |
| WO | WO 95/01139 | | 1/1995 | |

* cited by examiner

*Primary Examiner*—David H. Willse
*Assistant Examiner*—Alvin Stewart
(74) *Attorney, Agent, or Firm*—Townsend and Townsend and Crew LLP

(57) ABSTRACT

In a method for the releasing of an insert (3, 3a) from the shell (2, 2a) of an artificial joint pan (1, 1a) the insert (3, 3a) is firmly arranged in the shell (2, 2a) of the joint pan (1, 1a). It is removable from the shell (2, 2a) after the releasing from the shell (2, 2a). For the releasing of the insert (3, 3a) from the shell (2, 2a) a fluid is introduced between the insert (3, 3a) and the shell (2, 2a) which effects the releasing of the insert (3, 3a) from the shell (2, 2a).

9 Claims, 2 Drawing Sheets

METHOD FOR THE RELEASING OF AN INSERT FROM THE SHELL OF AN ARTIFICAL JOINT PAN AND ARTIFICAL JOINT PAN

BACKGROUND OF THE INVENTION

The invention relates to a method for the releasing of an insert from the shell of an artificial joint pan as well as to an artificial joint pan.

Artificial joint pans in general, but in particular however hip joint pans, which are implanted into the acetabulum of a patient, comprise as a rule the following essential parts: A shell on the one side which is mainly manufactured of titanium or of a titanium alloy in the case of cement-free implantation (in cemented implantation e.g. of a cobalt-chromium alloy) and an insert on the other side which can be placed into this shell and which is as a rule manufactured either of polyethylene or ceramic or is metallic. The insert has a joint surface on which the joint ball, in a hip joint pan the femur-side joint ball, is movable. During the implantation of an artificial hip joint pan of this kind the shell is typically first secured in the acetabulum—numerous kinds of securing are known for this. After the securing of the shell the insert is introduced into the shell, and indeed in such a manner that it is arranged in a fixed manner in the shell after the introduction.

The arranging in the shell in a fixed manner can take place in different ways: For inserts of polyethylene this can for example take place in that the insert (also called an "inlay") snaps in through a snap connection into the shell, thus in that two mutually undercutting parts slide past one another and in this way enter into a snap connection which cannot be released without special measures.

In the case of harder materials of the inserts such as ceramic or metal, cone connections are being used for some time now in which the fixed connection comes about with the help of a conical surface on the outer wall of the insert and a corresponding conical surface on the inner wall of the shell. The insert of ceramic or of metal respectively is held firmly in a clamping seat in the shell which cannot be released without special measures.

Even though joint pans of this kind are very durable and can also stand high stresses, it can however become necessary for various reasons to subject an artificial pan of this kind to a revision after some time. In this case one naturally does not wish to renew the entire joint pan, but merely the insert, because the shell is as a rule firmly and well connected to the bone material of the acetabulum. On the other hand however the insert is firmly connected to the shell and cannot simply be released from the shell without further ado.

In inserts of polyethylene (snap connection between the insert and the shell) the releasing of the insert from the shell—in the above-explained example thus the releasing of the snap connection—takes place for example in such a manner that an auxiliary tool is screwed through the polyethylene insert in accordance with the principle of the corkscrew. The front end of the auxiliary tool braces itself against the (titanium) shell when screwed further in and forces the insert out of the shell in that the mutually undercutting parts of the insert and the shell again slide past one another (against the restraining force of the snap connection), but this time however in the direction opposite to the insertion, through which the snap connection is released.

In inserts of harder materials such as ceramic or metal, which are firmly arranged in the shell via a cone clamping seat, other methods must be used. A known method for the releasing of a cone clamping seat of this kind consists in transmitting a striking impulse (for example using a suitable auxiliary tool) to the shell—but not to the insert however—through which the cone clamping seat is released.

It is immediately evident that both measures are not exactly convenient for the surgeon or orthopedist respectively who performs the operation. The screwing in of the auxiliary tool in polyethylene inserts is comparatively difficult. The releasing of ceramic or metal inserts by means of a striking impulse is likewise somewhat difficult because a corresponding auxiliary tool for the transmission of the striking impulse must first be applied to the pan and secured against a slipping off, and only then can the striking impulse be produced. Moreover, this procedure is such that the transmission of the striking impulse can have a negative effect on the bone matter. Moreover, it is also not ensured whether inserts which were inserted in the shell over a number of years ago in the body of a patient can reliably be released through the transmission of a striking impulse to the shell.

SUMMARY OF THE INVENTION

An object of the invention is thus to propose a simple and at the same time gentle and reliable method for the releasing of the insert from the shell which is suitable both for the releasing of inserts of polyethylene and for the releasing of inserts of harder materials such as ceramic or plastic. Furthermore, it is an object of the invention to propose a corresponding artificial joint pan.

This object is satisfied by introducing a fluid between the insert and the shell when releasing the insert from the shell, which facilitates the releasing of the insert from the shell. This is comparatively simple, as shall be explained more precisely, and also takes place without a stress for the surrounding bone tissue in which the shell is anchored. After the releasing of the insert, the insert can simply be removed from the shell and a new insert can be introduced into the shell.

A liquid, in particular a body compatible liquid, is preferably used as the fluid. This can for example be a body compatible cooking salt solution. In principle it is also possible to use a gas as the fluid; due to the incompressibility of liquids, however, a preference will be given to a liquid in the majority of cases.

Especially in the case of inserts of harder materials such as ceramic or metal it is regularly the case that when the insert is firmly introduced into the shell an intermediate space is still present between the base of the shell and the base of the insert. As a result of this, in one exemplary embodiment the fluid or the liquid respectively is introduced into this space between the base of the shell and the base of the insert until the insert is released from the pan, that is, the cone clamping seat is released. After the releasing of the insert from the shell the insert can then simply be removed from the shell and a new insert introduced.

In inserts of polyethylene the connection of the insert and the shell frequently consists in a snap connection near the base of the insert. The base of the insert of polyethylene rests more or less on the base of the shell, for which reason—in contrast to inserts of harder materials such as ceramic or metal—practically no space is present between the base of the shell and the base of the insert into which the fluid or the liquid can be introduced. For this reason a groove which is upwardly open, e.g. a ring groove, can be provided in the shell into which the fluid or the liquid respectively can be introduced. Through the fluid or the liquid respectively which is introduced into this groove (under pressure) the insert can be pressed out of the shell until the snap connection is released. After the releasing of the snap connection the insert can be removed from the shell in a simple manner.

In general it can thus be stated that in this variant the fluid or the liquid respectively is introduced into a space which extends beneath the base of the insert. This can—as described above—either be a space which extends between the base of the shell and the base of the insert (e.g. a cone clamping seat in inserts of harder materials) or an upwardly open groove which is provided in the shell, e.g. the named ring groove (e.g. in inserts of polyethylene resting on the base of the shell).

The fluid or the liquid respectively can also be introduced into a space between the side wall of the shell and the side wall of the insert, which is interesting in particular in the case of inserts of harder material such as ceramic or metal. This measure can take place either alone or in addition to the introduction of the fluid into the space between the base of the shell and the base of the insert.

DETAILED DESCRIPTION OF SPECIFIC EXEMPLARY EMBODIMENTS

Figure 1:
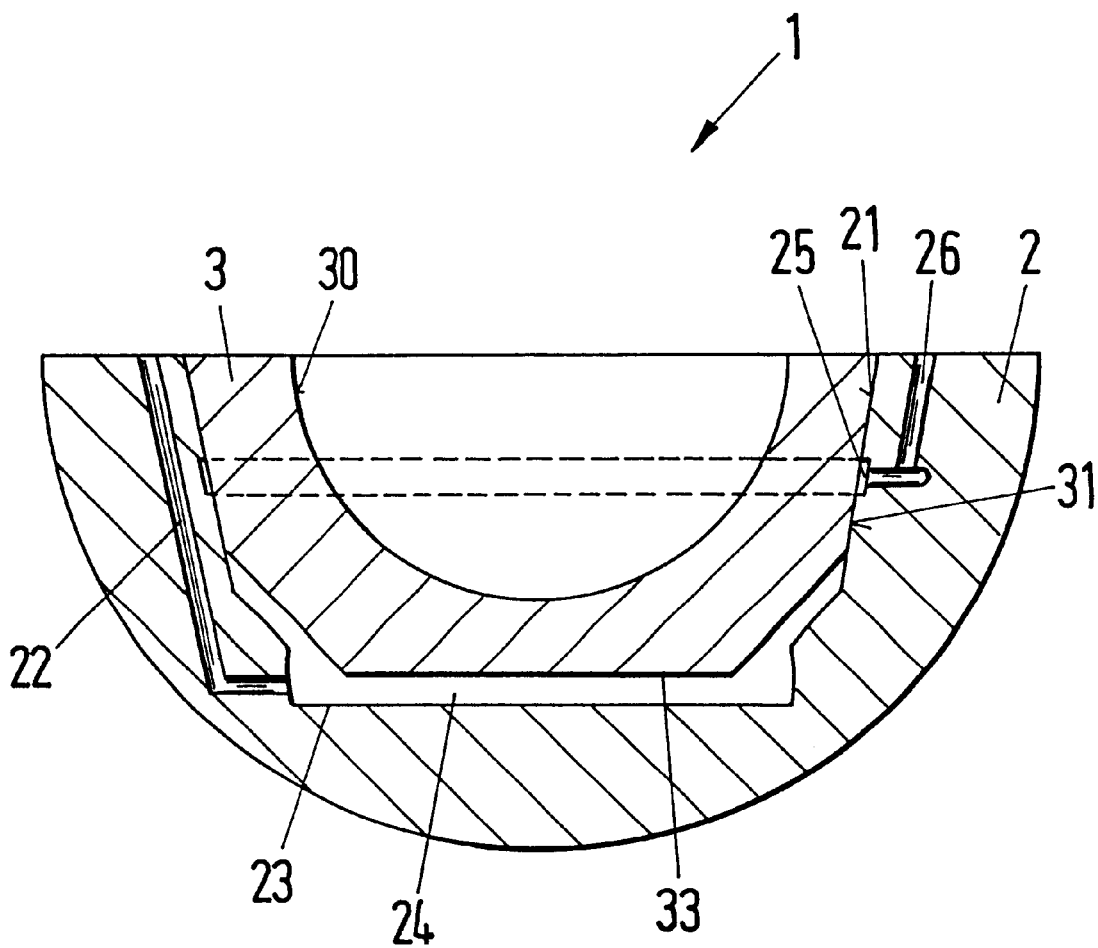
FIG. 1 is a section of an artificial hip joint pan with an insert of a harder material such as ceramic or metal, which is firmly arranged in the shell by means of a cone connection.

In FIG. 1 one recognizes an artificial joint pan, here an artificial hip joint pan 1, which comprises a shell 2 and an insert 3. The insert 3 is manufactured in this exemplary embodiment of a harder material, for example of ceramic or metal. It has a joint surface 30 on which the joint ball (not illustrated) at the femur side is movable. This joint surface 30 typically represents a section of a spherical surface.

The insert 3 is firmly arranged in the shell 2 with the help of a cone connection. This cone connection arises with the help of a conical surface of the side wall 31 (outer wall) of the insert 3 and of a corresponding conical surface of the side wall 21 (inner wall) of the insert 2. These form a clamping seating when the insert 3 is introduced into the shell 2 so that the insert 3 cannot be released from the shell 2 during a revision without special measures.

In order now to be able to release the insert 3 from the shell 2 in a simple manner and, above all, in a manner which avoids damage to the surrounding bone matter, a passage 22 (illustrated in broken lines) is provided in the shell 2 which, beginning at the end surface of the shell 2, extends up to a region near the base 23 of the shell 2. There the passage 22 opens into a space 24 which extends between the base 23 of the shell 2 and the base 33 of the insert 3.

Into this space 24 now the fluid, in particular a body compatible liquid such as for example a body compatible cooking salt solution, is introduced until the clamping seating of the cone connection between the side wall 31 of the insert 3 and the side wall 21 of the shell 2 is released. For this as a rule no impracticable pressure is required; the pressure amounts to at most several bar.

In addition a fluid can also be introduced into the space between the side wall 31 of the insert 3 and the side wall 21 of the shell 2. This space is formed for example by a circumferential groove 25 which is provided in the side wall 21 of the shell 2. Through a passage 26 the fluid, for example the named body compatible liquid, enters into the groove 25, first fills this groove 25 and then contributes to the cone clamping seat of the insert 3 in the shell 2 being released.

The measure of introducing the fluid into a circumferential groove 25, that is, into a space between the side wall 31 of the insert 3 and the side wall 21 of the shell 2, is basically independent of the measure of introducing the fluid between the base 23 of the shell 2 and the base 33 of the insert 3. Both measures can take place either individually or else together.

Figure 2:
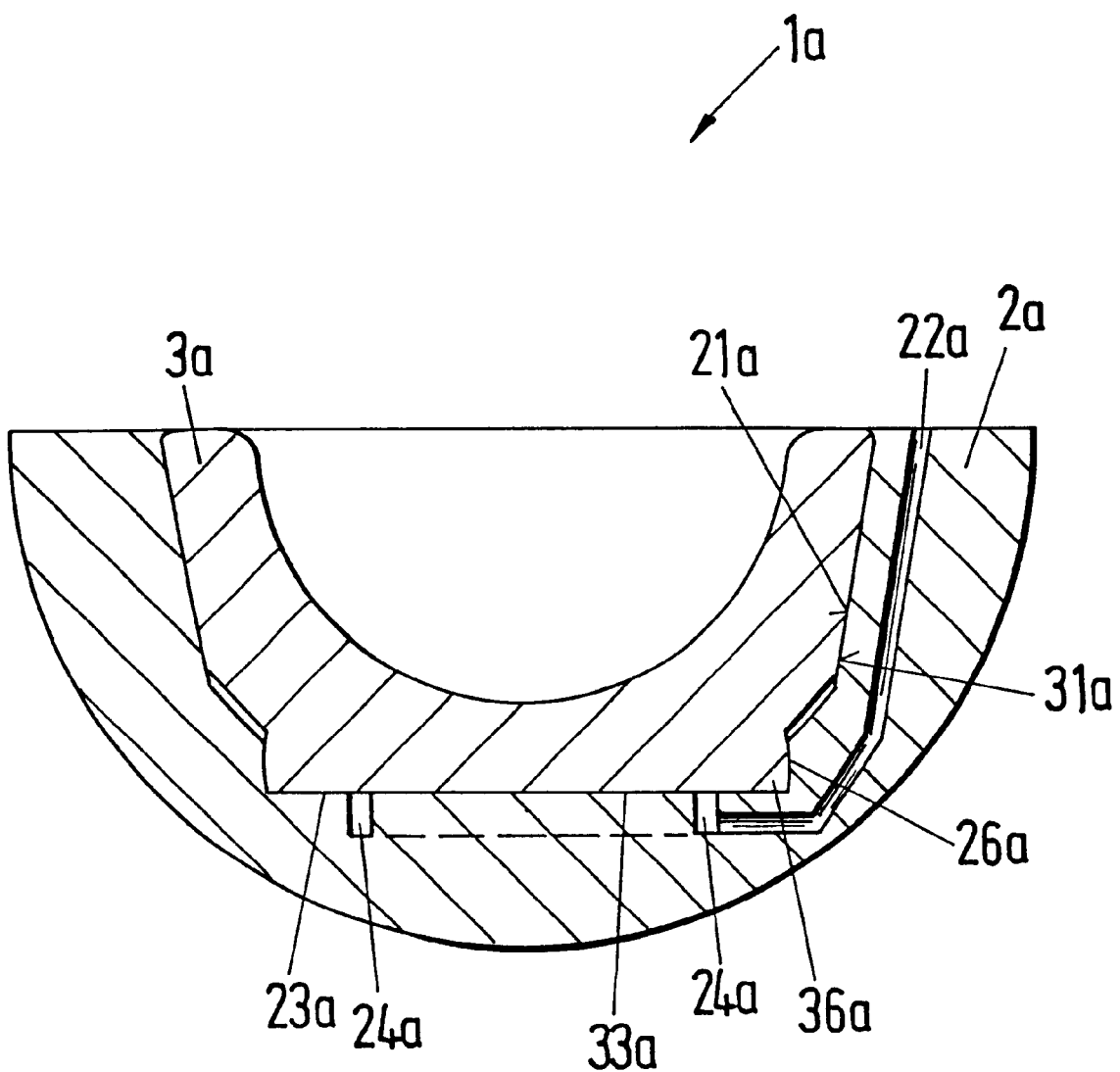
FIG. 2 is a section of an artificial hip joint pan with an insert of polyethylene, which is firmly arranged in the shell by means of a snap connection.

FIG. 2 shows an exemplary embodiment of an artificial joint pan, again a hip joint pan 1a, in which the insert 3a is firmly arranged in the shell 2a with the help of a snap connection. The snap connection is formed by mutually undercutting parts 36a at the insert 3a and 26a at the shell 2a. When the shell 2a is introduced, the undercutting parts 36a and 26a slide past one another, through which the snap connection "snaps in" and the insert 3a is firmly arranged in the shell 2a. As a securing against a rotation of the insert 3a with respect to the shell 2a, separate means (not illustrated) can be provided.

For the releasing of the insert 3a from the shell 2a the snap connection must be released; that is, parts 36a of the insert 3a and 26a of the shell 2a again slide along one another, but in the direction opposite to that in the introduction of the insert 3a. For this a passage 22a can be provided which opens into an upwardly open ring groove 24a which is provided in the shell 2a and extends beneath the base 33a of the insert 3a. In this exemplary embodiment of the artificial joint pan 1a, namely, the insert 3a extends substantially up to the base 23a of the shell 2a (in contrast to the case in the previously described exemplary embodiment), because of course the part 36a of the insert 3a must slide over the part 26a of the shell 2a in order to effect the snapping in of the snap connection. Through the supplying of a fluid, preferably of a body compatible liquid such as e.g. a body compatible cooking salt solution, through the passage 22a into the ring groove 24a the snap connection can be "opened" in that the part 36a of the insert 3a is forced to slide over the part 26a of the shell 2a. For this no impracticable pressure is required; the pressure amounts to at most several bar.

Nevertheless it is in principle also possible to provide the snap connection not in the vicinity of the base of the shell but rather further remote from the base. Then it is also possible to introduce the fluid—similarly as in the exemplary embodiment in accordance with FIG. 1—into a space between the base of the insert and the base of the shell, because then the base of the insert need not extend substantially up to the base of the shell. Naturally—similarly as in the exemplary embodiment in accordance with FIG. 1—a groove can also be provided in the side wall of the shell, into which liquid can be introduced in order to further facilitate the releasing out of the insert. The only measure for the releasing of the insert from the shell which is not suitable in this case is however a groove which is arranged in the side wall.

What is claimed is:

1. A method for releasing an insert from a shell of an artificial joint pan implanted into a human body, the insert being firmly arranged in the shell via a cone clamping seat and being removable from the shell after releasing from the shell, wherein for releasing of the insert from the shell, a fluid is introduced between the insert and the shell which effects the releasing of the insert from the shell.

2. A method in accordance with claim 1 including using a body-compatible liquid as the fluid.

3. A method in accordance with claim 1 wherein a space extends beneath a base of the insert, and including introducing the fluid into the space.

4. A method in accordance with claim 1 wherein a space is between a side wall of the shell and a side wall of the insert, and including introducing the fluid into the space.

5. An artificial joint pan implanted into a human body comprising a shell and an insert, wherein the insert is fixedly arranged in the shell via a cone clamping seat and wherein the joint pan is provided with means for introducing a fluid between the insert and the shell which effects a releasing of the insert from the shell.

6. An artificial joint pan in accordance with claim 5 wherein the shell and the insert are formed so that, with the insert being inserted in the shell, a space is formed which extends beneath the base of the insert, and including a passage extending from an end surface of the shell to the space beneath the base of the insert, the passage opening into the space.

7. An artificial joint pan in accordance with claim 5 wherein the shell and the insert are formed so that, with the insert inserted in the shell, a space is formed between a side wall of the shell and a side wall of the insert, and including a passage extending from an end surface of the shell to the space between the side wall of the insert and the side wall of the shell, the passage opening into the space.

8. A method of releasing an insert from a shell of an artificial joint pan implanted into a human body comprising arranging the insert in the implanted shell, securing the insert to the shell with a cone clamping seat so that the insert is firmly arranged in the shell when the cone clamping seat is engaged and is removable from the shell when the cone clamping seat is released, and introducing a fluid between the insert and the implanted shell which releases the cone clamping seat and thereby releases the insert from the implanted shell.

9. An artificial joint pan comprising a shell implanted into a human body, an insert arranged inside the shell, a releasable cone clamping seat cooperating with the shell and the insert and securing the insert to the shell to prevent an unintended separation of the insert from the shell, and means for introducing a pressurized fluid between the insert and the shell for exerting a force between the insert and the shell which releases the cone clamping seat and thereby releases the insert from the implanted shell.

* * * * *